United States Patent [19]

Couillard

[11] Patent Number: 4,769,141

[45] Date of Patent: Sep. 6, 1988

[54] LIQUID PHASE CHROMATOGRAPHY APPARATUS

[75] Inventor: Francois Couillard, Pau, France

[73] Assignee: Compagnie Europeenne D'Instrumentation (CEDI), Lannemezan, France

[21] Appl. No.: 120,135

[22] Filed: Nov. 13, 1987

[30] Foreign Application Priority Data

Nov. 13, 1986 [FR] France .................. 86 15724

[51] Int. Cl.$^4$ .......................... B01D 15/08
[52] U.S. Cl. .................... 210/198.2; 55/386
[58] Field of Search ............. 210/656, 657, 658, 659, 210/198.2; 55/67, 197, 386

[56] References Cited

U.S. PATENT DOCUMENTS

| | | | |
|---|---|---|---|
| 3,487,938 | 1/1970 | Patterson | 210/198.2 |
| 3,682,315 | 8/1972 | Haller | 210/198.2 |
| 4,280,905 | 7/1981 | Gunkel | 210/198.2 |
| 4,476,017 | 10/1984 | Scharff | 210/198.2 |
| 4,497,711 | 2/1985 | Shepherd | 210/198.2 |
| 4,565,632 | 1/1986 | Hatch | 210/198.2 |
| 4,597,866 | 7/1986 | Couillard | 210/352 |
| 4,636,316 | 1/1987 | Harris | 210/198.2 |
| 4,655,917 | 4/1987 | Shackelford | 210/198.2 |

Primary Examiner—Ernest G. Therkorn
Attorney, Agent, or Firm—Browdy and Neimark

[57] ABSTRACT

A liquid phase chromatography apparatus consists of a tubular column which is intended to receive a charge of powdery adsorbing solid material and which comprises porous plates at its ends, one of these plates being fastened there and other plate being able to move inside the column under the action of a jack and thus to compress the charge in the column. This apparatus is characterized in that charge (5) is contained in an interchangeable rigid or semi-rigid cartridge (4) with an outside diameter approximately equal to the inside diameter of column (1), the latter being cut into two equal half-cylinders (2) which are brought together after insertion of said cartridge (4) and which are kept clamped together by any suitable means (3).

20 Claims, 1 Drawing Sheet

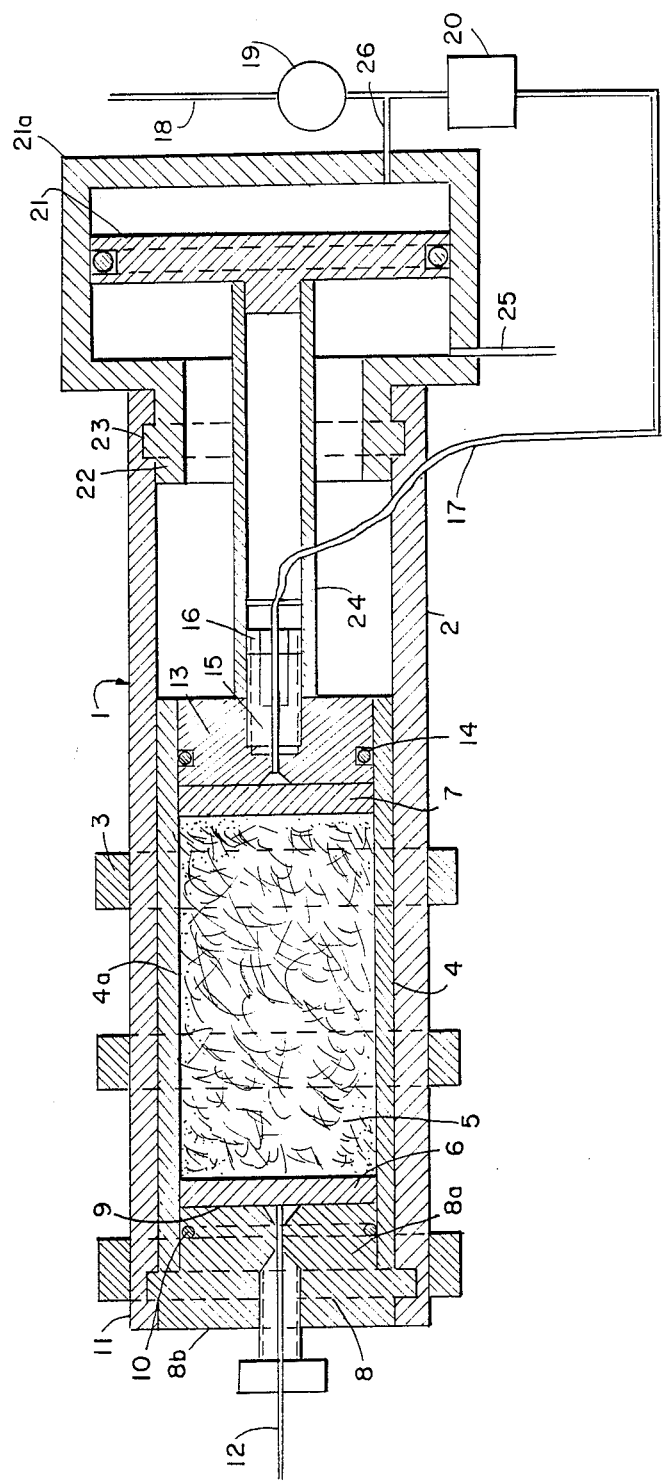

LIQUID PHASE CHROMATOGRAPHY APPARATUS

BACKGROUND OF INVENTION

1. Field of Invention

This invention has as its object a liquid phase chromatography apparatus consisting of a tubular column which is intended to receive a charge of powdery solid material and which comprises porous plates at its ends, one of these plates being fastened there by suitable means and another plate being able to move inside the tube under the action of a jack and thus compress the charge in the column.

2. Description of the Prior Art

A chromatography apparatus of this type is already known and is described in French patent application No. 83/19315 of Dec. 2, 1983. This apparatus operates satisfactorily, but it still has two drawbacks:

Putting the column into operating condition requires the powder of adsorbing particles first to be poured either in bulk or in suspension into a liquid. The column must then be closed with a porous plate, acting as a cover, before moving the other porous plate under the action of the jack;

At the end of chromatography, when it is desired to recover intact the charge of adsorbing powder at the various "altitudes" at which are adsorbed the various components of the mixture analyzed by passage in the column, the delicate removal of the powder charge from the column is necessary.

SUMMARY OF THE INVENTION

The object of the present invention is to remedy these drawbacks and to achieve a chromatography apparatus which makes it possible to put the column into operation quickly, which facilitates intact recovery of the adsorbing charge, and which is simple and inexpensive to make.

According to the invention, these objects, and others which will become apparent upon reading the present specification, are attained using a liquid phase chromatography apparatus of the type specified above, which is characterized in that the charge is contained in a rigid or semi-rigid cartridge with an outside diameter approximately equal to the inside diameter of the column, the latter itself being cut into two equal half-cylinders which are brought together after insertion of the cartridge and which are kept clamped together around the cartridge by any suitable means.

Thus a column ready for use is available, and since the cartridge containing the charge undergoes practically no deformations during operation, recovery of the unit formed by the cartridge, the charge and the analyzed or prepared products is extremely easy, so that the column can be reused in a short period for a new processing.

Because the charge of adsorbing material is held in the cartridge by porous plates, and not directly in the column, it is possible to put these plates in place and to charge the cartridge with adsorbing powder well before its insertion in the column, for example, at the powder or cartridge manufacturer. Handling, shipping and storing of the charged cartridges is then very simple.

At each of its ends, the inside of the column comprises annular grooves intended to receive corresponding shoulders which are made on the heads of the columns to fix their positions during operation of the column.

It is advantageous for one of the column heads to end in a piston with an outside diameter approximately equal to the inside diameter of the cartridge, an annular groove being made in the lateral surface of this piston to receive a seal.

Advantageously, the other column head consists of a jack which comprises a tubular brace provided at its ends with two pistons, of which the first is practically identical with the piston terminating the first column head, the second of these pistons being able to slide in a compression cylinder with an inside diameter greater than that of the cartridge, which is extended in the direction of the column by a sleeve with an outside diameter approximately equal to the inside diameter of the column and provided on the inside with a shoulder intended to engage in a corresponding annular groove of the inside of the column, the first of these pistons comprising an axial passage connected to a supply tube and passed through by the liquid to be analyzed or prepared.

In an advantageous embodiment of the invention, a tip is axially screwed into a first piston specified above, a connector in turn being mounted on this tip and connected to the liquid supply tube, the latter going through the walls of the brace and the column to come out from the latter and extending to the cartridge by an axial passage made through the connector, the tip and first cylinder to allow the liquid that is to be analyzed or prepared to circulate between an outside tank and the cartridge according to the invention.

Preferably, the liquid supply tube is connected to a pipe which is connected to the outside tank and on which a pump and injector are mounted. Advantageously, the chamber of the compression cylinder which is opposite the column is connected to the supply tube in question between its pump and its injector, the other chamber of this cylinder being connected to the atmosphere.

BRIEF DESCRIPTION OF THE DRAWING

The following description, which is not intended to be limiting, will give a better understanding of how the invention can be embodied. It should be read with reference to the accompanying drawing, whose single figure represents a view in longitudinal section of the chromatography apparatus according to the invention.

DETAILED DESCRIPTION OF THE EMBODIMENT

As can be seen in the figure, the column which is designated as a whole by reference 1, consists of two half-shells 2 of which only one is represented in the figure, the other half-shell being of a shape and structure exactly the same as or similar to the first. Their joining forms a cylinder which is kept assembled by any suitable means such as locking rings 3 surrounding column 1, or also by flanges assembled by screws.

On the inside of column 1 is placed a cartridge 4 of rigid or semi-rigid material whose outside diameter is approximately equal to the inside diameter of the cylinder formed by the two half-shells 2. It contains a charge of adsorbing material 5 in powder or in suspension in a liquid which is enclosed between porous plates 6 and 7 in the form of disks, the first, 6, at the left of the figure, being fastened to case 4a of cartridge 4 by suitable means (not shown), and the second, 7, on the right of the figure, being able to move toward the inside of cartridge 4, as will be explained in more detail below.

When cartridge 4 is in place inside column 1, porous plate 6 rests on a first column head 8 which closes the latter and which comprises two parts 8a and 8b of different diameters. Part 8a is inserted in case 4a of cartridge 4, its outside diameter being very slightly less than the inside diameter of this case. On its front part 9 rests porous plate 6, an O-ring 10 being housed in a groove made in head 8 to assure the seal between the latter and case 4a of cartridge 4.

Other part 8a of column head 8, whose outside diameter is approximately equal to the inside diameter of column 1 in which it is inserted, exhibits an annular shoulder 11 which, during assembly of the two half-shells 2 of column 1, is housed in a groove of complementary shape made in the inside wall of column 1.

An axial duct 12 going through column head 8 allows the liquid which is to be analyzed or prepared to flow to the outside from the cartridge, through porous plate 6.

Column head 13 exhibits an outside diameter equal to the inside diameter of case 4a of cartridge 4 in which it can slide, an O-ring 14 housed in a groove of corresponding shape of head 13 assuring the seal between the latter and case 4a of cartridge 4.

An axial tip 15 is screwed into column head 13. It projects outward and receives a connector 16 on which is mounted, by any suitable means, the end of a flexible tube 17 which makes it possible to inject into cartridge 4, through a passage made in the axis of connector 16, of tip 15 and head 13, the liquid which is to be analyzed or prepared, which comes from a tank (not shown) through a supply pipe 18 on which are mounted a pump 19 and an injector 20. However, it would also be possible to bring the liquid by duct 12, to the other end of column 1, and evacuate it by tube 17.

The part of tip 15 which projects beyond head 13 is covered by a tubular brace 24 which, at its other end, is solid with a piston 21 whose diameter is greater than that of column 1. This piston 21 moves axially in a compression cylinder 21a extended to column 1 by a sleeve 22 whose outside diameter is approximately equal to the inside diameter of column 1 into which it is pushed and held in place by an annular shoulder 23 which, during assembly of the two half-shells 2, is housed in a groove of complementary shape which is made in the lateral inside surface of column 1.

Finally, tubular brace 24, mounted between column head 13 and piston 21, limits the travel of the latter toward cartridge 4, and can consist of two half-columns assembled by any suitable means which facilitates charging of column 1, while compression cylinder 21a comprises a pipe 25 for connection with the atmosphere, coming out on the face of piston 24 which is turned toward column 1, as well as an intake 26 of liquid under pressure which comes out on the other face of piston 21, this liquid being intended to move piston 21 and thus to compress charge 5 of cartridge 4 by means of brace 24 and porous plate 7. This liquid can be the vector liquid itself which is injected in cartridge 4, in which case intake pipe 26 is connected to supply pipe 18 between pump 19 and injector 20. The diameter of piston 21 being greater than that of column 1, it is understood that thus a hydraulic amplification is obtained which makes possible an axial self-compression of the contents of cartridge 4 which is always more intense than the force applied on the column heads by the liquid on the inside of the cartridge. However, it is possible to provide another source of pressure for piston 21.

It will be easily understood that the length of tubular brace 24 should be selected as a function of that of cartridge 4 so that piston 21 can have the desired travel inside cylinder 21a. Moreover, this makes possible the use of cartridges of different lengths: when the length of the cartridge is changed, it suffices to select a new brace 24 so that the sum of its length and that of the new cartridge remains almost unchanged relative to the preceding processing.

What is claimed is:

1. In a liquid phase chromatography apparatus comprising a tubular column, with two ends, for receiving a charge of powdery solid material, a porous plate on each of said ends, one of said plates being fastened thereon and the other plate being able to move axially inside the column by means of a jack to thus compress the charge in the column, the improvement wherein comprising said charge (5) being contained in a removable rigid or semi-rigid cartridge (4) with an outside diameter approximately equal to the inside diameter of column (1), the column being formed by two divisible half-cylinders (2) which are clamped together around said cartridge (4).

2. Chromatography apparatus according to claim 1, wherein the inside of column (1) comprises, at each of its ends, annular grooves for receiving corresponding washers or shoulders (11, 23), respectively, of a column head (8) or said jack (22), respectively, to fix their position during operation of the column.

3. Chromatography apparatus according to claim 2, comprising at an end thereof, a column head (8) terminated by a piston (8a) with an outside diameter approximately equal to the inside diameter of cartridge (4), an annular groove being made in the lateral surface of said piston (8a) for receiving a seal (10).

4. Chromatography apparatus according to claim 2 comprising, at one end thereof, a column head including said jack (22), said jack (22) comprising a tubular brace (24), said tubular brace (24) having two ends, the ends being provided with first and second pistons (13, 21), respectively, said first piston (13), positioned at an end of said column head proximal to said column (1), being slidable within said cartridge (4), said second piston (21), located at an end of said column head distal to said column (1), being slidably positioned within a compression cylinder (21a) with an inside diameter greater than that of cartridge (4), said compression cylinder (21a) being extended in the direction of column (1) by a sleeve (22) with an outside diameter approximately equal to the inside diameter of column (1) and provided on the inside with a shoulder (23) for engaging in a corresponding annular groove of the inside of column (1), the first (13) of said pistons comprising an axial passage connected to a supply tube (17) through which liquid to be analyzed or prepared passes.

5. Chromatography apparatus according to claim 2, wherein said cartridge (4) is pre-assembled and pre-filled.

6. Chromatography apparatus according to claim 1 comprising at an end thereof, a column head (8) terminated by a piston (8a) with an outside diameter approximately equal to the inside diameter of cartridge (4), an annular groove being made in the lateral surface of said piston (8a) for receiving a seal (10).

7. Chromatography apparatus according to claim 6 comprising, at one end thereof, a column head including said jack (22), said jack (22) comprising a tubular brace (24), said tubular brace (24) having two ends, the ends being provided with first and second pistons (13, 21), respectively, said first piston (13), positioned at an end of said column head proximal to said column (1), being slidable within said cartridge (4), said second piston (21), located at an end of said column head distal to said column (1), being slidably positioned within a compression cylinder (21a) with an inside diameter greater than that of cartridge (4), said compression cylinder (21a) being extended in the direction of column (1) by a sleeve (22) with an outside diameter approximately equal to the inside diameter of column (1) and provided on the inside with a shoulder (23) for engaging in a corresponding annular groove of the inside of column (1), the first (13) of said pistons comprising an axial passage connected to a supply tube (17) through which liquid to be analyzed or prepared passes.

8. Chromatography apparatus according to claim 6, wherein said cartridge (4) is pre-assembled and pre-filled.

9. Chromatography apparatus according to claim 1 comprising, at one end thereof, a column head including said jack (22), said jack (22) comprising a tubular brace (24), said tubular brace (24) having two ends, the ends being provided with first and second pistons (13, 21), respectively, said first piston (13), positioned at an end of said column head proximal to said column (1), being slidable within said cartridge (4), said second piston (21), located at an end of said column head distal to said column (1), being slidably positioned within a compression cylinder (21a) with an inside diameter greater than that of cartridge (4), said compression cylinder (21a) being extended in the direction of column (1) by a sleeve (22) with an outside diameter approximately equal to the inside diameter of column (1) and provided on the inside with a shoulder (23) for engaging in a corresponding annular groove of the inside of column (1), the first (13) of said pistons comprising an axial passage connected to a supply tube (17) through which liquid to be analyzed or prepared passes.

10. Chromatography apparatus according to claim 9, wherein a tip (15) is screwed axially into said first piston (13), a connector (16) in turn being mounted on said tip (15) and connected to said supply tube (17), said supply tube extending through said brace (24) and wall (2) of said column (1) to extend therebeyond, and which is extended from said tip (15) to cartridge (4) by an axial passage made through said connector (16), said tip (15) and said first cylinder (13), to allow the circulation of the liquid which is to be analyzed or prepared from an outside tank.

11. Chromatography apparatus according to claim 10, wherein said supply tube (17) is connected to a supply pipe (18) which is connected to said outside tank of liquid to be analyzed or prepared and on which are mounted a pump (19) and an injector (20).

12. Chromatography apparatus according to claim 11, wherein a portion of said compression chamber (21a) facing a side of said second piston (21) distal to said column (1), is connected by a pipe (26) to said supply pipe (18) between pump (19) and injector (20), while a pipe (25) for connection to the atmosphere is connected to a portion of said compression chamber (21a) facing a side of said second piston (21) proximal to said column (1).

13. Chromatography apparatus according to claim 12, wherein the length of said brace (24) is selected is a function of that of said cartridge.

14. Chromatography apparatus according to claim 11, wherein the length of said brace (24) is selected as a function of that of said cartridge (4).

15. Chromatography apparatus according to claim 10, wherein the length of said brace (24) is selected as a function of that of said cartridge (4).

16. Chromatography apparatus according to claim 10, wherein said cartridge (4) is pre-assembled and pre-filled.

17. Chromatography apparatus according to claim 9, wherein said cartridge (4) is pre-assembled and pre-filled.

18. Chromatography apparatus according to claim 9, wherein the length of said brace (24) is selected as a function of that of said cartridge (4).

19. Chromatography apparatus according to claim 1, wherein said cartridge (4) is pre-assembled and pre-filled.

20. Chromatography apparatus according to claim 19, wherein the length of said brace (24) is selected as a function of that of said cartridge.

* * * * *